United States Patent [19]

Kitney et al.

[11] Patent Number: 5,520,192
[45] Date of Patent: May 28, 1996

[54] APPARATUS FOR THE MONITORING AND CONTROL OF RESPIRATION

[75] Inventors: Richard I. Kitney; Simon Bignall, both of London, Great Britain

[73] Assignee: Imperial College of Science, Technology and Medicine, London, England

[21] Appl. No.: 345,332

[22] Filed: Nov. 21, 1994

Related U.S. Application Data

[63] Continuation of Ser. No. 46,869, Apr. 8, 1993, abandoned, which is a continuation-in-part of Ser. No. 842,319, Feb. 28, 1992, abandoned.

[30] Foreign Application Priority Data

Dec. 23, 1991 [GB] United Kingdom ............... 9127272

[51] Int. Cl.$^6$ ................................................ A61B 5/08
[52] U.S. Cl. ................................................ 128/716
[58] Field of Search ............... 128/716, 720–727, 128/670, 671, 204.21, 204.23, 202.22

[56] References Cited

U.S. PATENT DOCUMENTS

| | | | |
|---|---|---|---|
| 3,478,746 | 11/1969 | Greatbatch | 607/9 |
| 3,842,828 | 10/1974 | Bird | 128/202.22 |
| 4,323,064 | 4/1982 | Hoenig et al. | |
| 4,667,669 | 5/1987 | Pasternack | 128/202.22 X |
| 4,671,297 | 6/1987 | Schulze, Jr. | 128/721 X |
| 4,686,974 | 8/1987 | Sato et al. | |
| 4,945,899 | 8/1990 | Sugiyama et al. | 128/721 X |
| 4,972,842 | 11/1990 | Korten et al. | 128/200.24 X |
| 5,165,397 | 11/1992 | Arp | 128/204.21 |

OTHER PUBLICATIONS

R. I. Kitney, "Techniques for Studying Short–Term Changes in Cardio–Respiratory Data", Blood Pressure and Heart Variability, IOS Press 1993 pp. 1–23.

Primary Examiner—Angela D. Sykes
Assistant Examiner—Samuel Gilbert
Attorney, Agent, or Firm—Cushman, Darby & Cushman

[57] ABSTRACT

A respiration monitor for measuring the respiration of a subject on a mechanical ventilator comprises first transducer means arranged to produce a first signal representative of a respiration status of the subject, second transducer means arranged to produce a second signal representative of a cyclical status of the mechanical ventilator, and processor means arranged to receive said first and second signals and to produce an output signal dependent upon the relative phase of said first and second signals. The invention extends to a method of monitoring, and also to a method of determining the rate at which a mechanical ventilator should be set in order to achieve 1:1 entrainment with spontaneous respiratory efforts.

36 Claims, 12 Drawing Sheets

APPARATUS FOR THE MONITORING AND CONTROL OF RESPIRATION

This is a continuation of application Ser. No. 8/46,869, filed on Apr. 8, 1993, which was abandoned upon the filing hereof and which was a CIP of application Ser. No. 07/842,319 filed Feb. 28, 1992 now abandoned.

FIELD OF THE INVENTION

The present invention relates to a method and apparatus for the monitoring and control of a subject's physiological status (e.g. respiration). It finds particular (although not exclusive) application in monitoring and controlling chaotic activity during ventilation of newly born infants, and in the provision of a visual display which is suitable for diagnostic purposes.

BACKGROUND OF THE INVENTION

Patients with severe respiratory illness may require assistance with their breathing if their lungs are stiff, the respiratory muscles weak, or if oxygenation of the blood is inadequate due to lung disease. Respiratory assistance is given by blowing air/oxygen mixtures into the lungs using a mechanical ventilator to expand the lungs and take over some, or all, of the work of breathing.

Patients who are often breathing spontaneously during mechanical ventilation may "fight the ventilator" when they are trying to breathe at different times from the action of the ventilator. This creates problems in the exchange of gases in the lungs, can lead to sudden changes in the action of the heart and in the blood pressure, and can affect the flow of blood to the brain when the patients are severely ill. These adverse effects of "fighting the ventilator" are seen most dramatically in the sick, prematurely born infant. These tiny infants are at risk from brain damage when their breathing patterns become disordered, and more efficient methods of mechanical ventilation are constantly being sought for this group. Rapid changes in clinical state, irritability and the presence of airway reflexes lead to complex and rapidly changing interactions between the baby and the mechanical ventilator. Muscle paralysis is used to suppress spontaneous respiratory efforts, but may be associated with cardiovascular compromise and the need for higher inflating pressures. New techniques of mechanical ventilation attempt to induce and maintain phase-locking or phase-synchrony by the use of fast rates and short inspiratory times, or by triggering ventilator inflation using sensors to detect diaphragmatic excursion. In clinical practice, mechanical ventilation of the newborn is hampered by an inability to assess baby-ventilator interactions by clinical observation at the high spontaneous respiratory frequencies seen (typically 1–2 Hz). Spontaneous respiratory activity is frequently erratic and accompanied by unpredictable activity such as hiccoughs, gasps and responses to painful and other stimuli. An ideal respiratory monitoring system would be able to track the phase, amplitude and frequency of spontaneous respiratory activity relative to mechanical inflation from breath to breath.

The physiological interactions underlying cardiorespiratory control are usually non-linear in nature. Entrainment of biological oscillatory rhythms, such as spontaneous respiratory activity, can be achieved under certain conditions by the application of a periodic stimulus, such as mechanical ventilation, provided that sufficient afferent information reaches the rhythm generator to bring about entrainment. During stable entrainment the output frequency of the spontaneous oscillator will be drawn into simple integer relationships with that of the periodic stimulus, and a fixed phase relationship will be maintained indefinitely, provided stochastic noise is minimal.

In order to achieve an adequate description of the complex changes which characterise the response of stimulated nonlinear systems in physiology we have developed a method (the frequency tracking locus) of tracking cycle-by-cycle changes as opposed to the steady state response. The advantage of the frequency tracking locus method is that it allows a quantitative estimate of the state of entrainment in a stimulated system, as well as providing a visualisation of the interactions between the stimulus and the output from the system.

The frequency response of a linear system may be determined by applying sinusoids of a fixed frequency and calculating the amplitude and phase difference between input and output. The steady-state frequency response of the system can be determined over its entire range by applying input sinusoids incrementally. In nonlinear oscillatory systems the input and output do not exhibit either a fixed amplitude ratio or phase relationship.

A key factor in the analysis of the interaction of nonlinear oscillations is the ability to track frequencies and transients in both stimulus and output signals. Under steady state conditions frequency tracking can be achieved by the use of Fourier estimators, but as entrainment of a nonlinear oscillator becomes unstable, the output oscillation becomes non-stationary. The Fourier integral is based on the assumption that the data extend over an infinite range without any change in frequency content i.e. the waveform is stationary. In practice this condition is never met, but accurate, practical frequency resolution can be achieved with a minimum of approximately 3 to 5 cycles of the fundamental frequency (the lowest frequency in the waveform). Consequently, Fourier estimation has been successful in those biological studies where experimental design has determined the stationarity of the frequency content. Examples of such studies include monitoring thermal entrainment of physiological rhythms, heart rate variability, controlled breathing experiments and observations of the effects of respiration on blood pressure in the newborn. When studies of physiological systems involve the analysis of spontaneous activity, however, it is known that nonlinearities in the control structure induce non-stationarities in the associated waveforms. Hence, Fourier estimators are unable to track the shorter periods of stationarity which occur. In this case we and others have applied linear estimation methods which can resolve over stationary data lengths of 1.5 cycles of the fundamental. While these methods have proved useful, they have two principal disadvantages in relation to the study of nonlinear oscillations. First, a great deal of care must be taken to define parameters such as model order, which can profoundly affect the behaviour of linear estimators. Results from the use of different model orders should be interpreted with extreme caution. Second, transient interactions cannot be defined by this approach. Unstable states of entrainment are characterised by significant non-stationarity in the response of a system, during which relationships change from cycle to cycle and even autoregressive spectral estimation will fail. The frequency tracking locus (as described below) is specifically designed for these conditions and can give cycle by cycle descriptions of the phase-amplitude parameter space and its variation with time.

The rhythmical neuronal activity responsible for spontaneous respiratory drive and the effects upon it of periodic lung inflations have been modelled using forced, non-linear equations. Where patients are allowed to breathe spontaneously during mechanical ventilation, such as in the sick newborn infant, stable entrainment is difficult to achieve. Studies of interactions between spontaneous respiratory activity and mechanical ventilators in adult humans and in animal models have revealed that entrainment of spontaneous respiration by the ventilator stimulus can occur under favourable conditions. In adults and animals entrainment appears to be induced by the activity of reflexes: the Hering-Breuer inflation reflex (which shortens spontaneous inspiration when inflation occurs during inspiration) and the Hering-Breuer deflation reflex (which lengthens expiration when inflation occurs during spontaneous expiration). Vagotomy abolishes entrainment, demonstrating the essential role of pulmonary reflexes mediated by parasympathetic pathways. Respiratory reflexes similar to those inducing entrainment in adults are present in the neonate.

SUMMARY OF THE INVENTION

According to a first aspect of the present invention there is provided a monitor for monitoring the physiological status of a subject connected to an apparatus for providing the subject with artificial physiological stimulation, the monitor comprising first transducer means arranged to produce a first signal representative of a physiological status of the subject, second transducer means arranged to produce a second signal representative of a cyclical status of the said apparatus, and processor means arranged to receive said first and second signals and to produce an output signal dependent upon the relative phase of said first and second signals.

According to a second aspect of the present invention there is provided a respiration monitor for monitoring the respiration of a subject on a mechanical ventilator, the monitor comprising first transducer means arranged to produce a first signal representative of a respiration status of the subject, second transducer means arranged to produce a second signal representative of a cyclical status of the mechanical ventilator, and processor means arranged to receive said first and second signals and to produce an output signal dependent upon the relative phase and/or amplitude of said first and second signals.

According to a third aspect of the present invention there is provided a method of monitoring the physiological status of a subject connected to an apparatus for providing the subject with artificial physiological stimulation, the method comprising using first transducer means to produce a first signal representative of a physiological status of the subject, using second transducer means to produce a second signal representative of a cyclical status of the said apparatus, and using processor means to produce an output signal which is dependent upon the relative phase of said first and second signals.

According to a fourth aspect of the present invention there is provided a method for monitoring the respiration of a subject on a mechanical ventilator, the method comprising using first transducer means to produce a first signal representative of the respiration status of the subject, using second transducer means to produce a second signal representative of a cycle status of the mechanical ventilator, and using processor means to produce an output signal which is dependent upon the relative phase of said first and second signals.

All of the compatible features set out in the specific description and the claims (not directly related to respiration) can be used with the invention in its broadest sense. In particular, the frequency-tracking locus can be used for many other cyclical physiological signals (eg heartbeat etc).

In one preferred arrangement, a feedback mechanism is provided whereby the frequency of the ventilator is controlled in dependence upon the relative phase of the first and second signals, and preferably in dependence upon the value for the time being of the path length index (PLI).

If the mechanical ventilator with which the apparatus of the present invention is to be used is capable of intermittent mandatory ventilation (IMV) the clinician can determine the frequency of mechanical ventilation for 1:1 entrainment with the subject's spontaneous respiratory efforts. The prediction determined by the spontaneous inter breath inverval (IBI) during IMV has been found to substantially more accurate than the IBI without any mechanical ventilation at all. Accordingly, in this aspect, the invention has improved the ability to predict the rate at which a mechanical ventilator should be set in order to achieve a prolonged state of 1:1 entrainment with spontaneous respiratory efforts.

A further advantage is that ventilation is continued at a low rate (using IMV) while the necessary calculations are performed, thus avoiding the deterioration in condition caused by the previously known method of discontinuing mechanical ventilation entirely in order to calculate spontaneous breathing frequency.

Preferably, the onset of spontaneous inspiration is detected, and this is used to create a signal which triggers the inflation phase of the ventilator.

The major problems of patient-triggered ventilation are:
1) inability of patient to "trigger" ventilator due to respiratory muscle fatigue, extreme prematurity, reduced central drive to respiration,
2) "autotriggering" i.e. mechanical inflations initiated by "noise" rather than by actual patient effort, and
3) delay in onset of mechanical inflation following the start of spontaneous inspiratory effort, usually due to inadequate sensor placement, system delay (physical, biological and electronic).

The preferred monitoring system can:
a) assess phase angle between trigger events and the onset of mechanical inflation (used to adjust sensitivity and sensor placement/type),
b) detect "autotriggering" by showing loss of respiratory effort and excessive regularity of spontaneous respiration, and
c) reveal inadequate detection of spontaneous inspiratory effort due to inappropriate settings of gain, or very irregular respiratory effort which may indicate airway blockage, or the need for sedation.

BRIEF DESCRIPTION OF THE DRAWINGS

The invention may be carried into practice in a number of ways and one specific embodiment will now be described, by way of example, with reference to the drawings, in which:

FIG. 3c shows the frequency tracking locus corresponding to the traces of FIG. 3a;

FIG. 4c shows the frequency tracking locus corresponding to the traces of FIG. 4a;

FIG. 5c shows the frequency tracking locus corresponding to the traces of FIG. 5a;

DESCRIPTION OF PREFERRED EMBODIMENTS

Figure 1A:
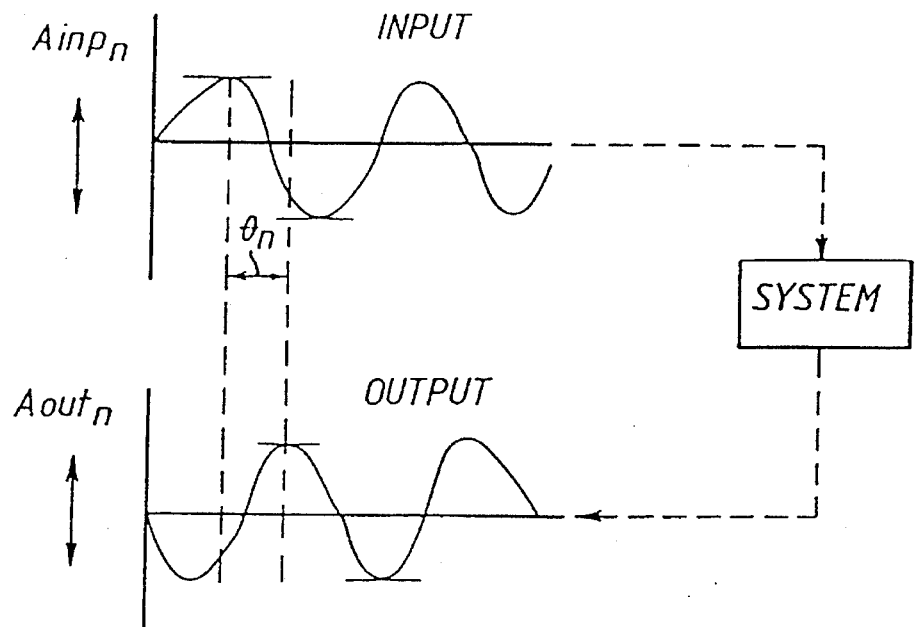
FIGS. 1a and 1b are explanatory diagrams showing the use of the frequency tracking locus for comparing the output and stimulus signals in a nonlinear system.

Referring now to the drawings, FIG. 1a shows in schematic form a comparison of the output and stimulus signals occurring in a nonlinear system in which the two signals vary in relative amplitude and phase difference on a cycle by cycle basis. For each cycle of the stimulus and output, an amplitude ratio $M_n$, and a phase difference $\Theta_n$ are obtained. $M_n$ is defined as the ratio of the amplitude of the output waveform to the input waveform for each cycle, in other words:

$$M_n = \frac{A_{out\ n}}{A_{inp\ n}}$$

Figure 1B:
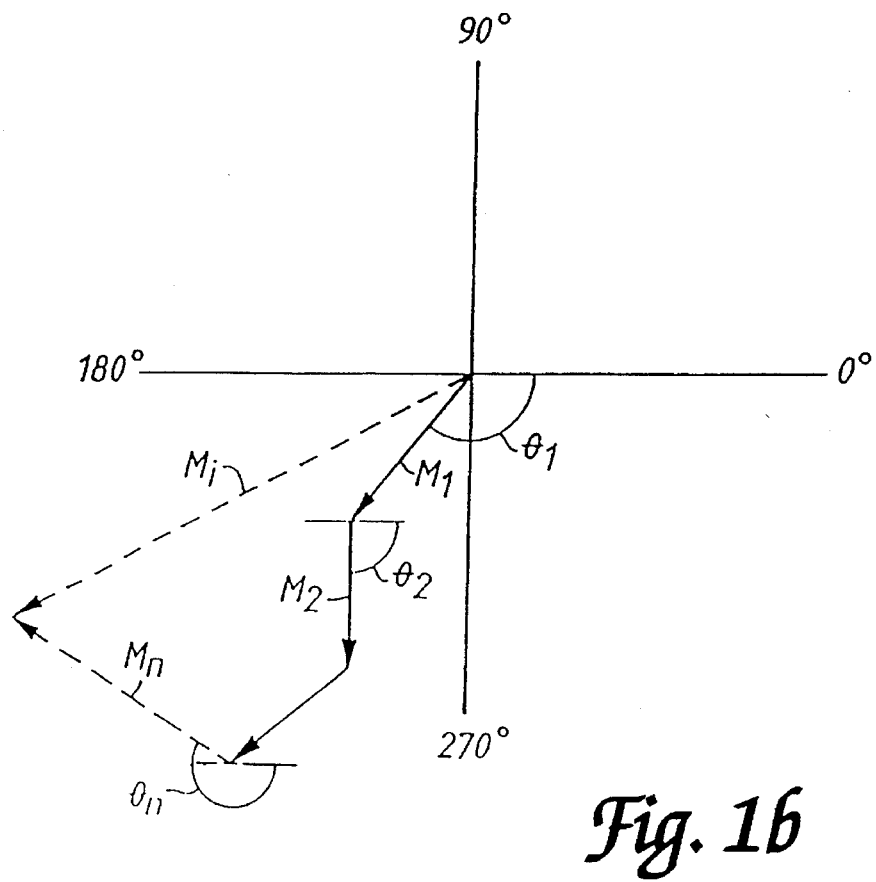

The values of $M_n$ and $\Theta_n$ are plotted as phasors on an Argand diagram (FIG. 1b). The first phasor starts at the origin, and each subsequent phasor is then plotted from the tip of the preceding phasor. Thus, each cycle is represented as a phasor describing the relative amplitude and phase of the output to the input signal. Under conditions of stable entrainment the individual cycle phasors will align. With a reduced influence of the stimulus, entrainment will become unstable and the individual phasors will vary both in length and direction.

In order to quantify the degree of departure from stable entrainment a single parameter (the path length index) is used. The path length index (PLI) is calculated as follows:

$$PLI = \frac{1}{M_i} \sum_{n=1}^{k} M_n$$

Where $M_i$=the length of the line from the origin to the tip of the terminal phasor.

For stable entrainment the path length index will be close to unity, and the index will progressively increase as the degree of chaos increases.

In the context of the present invention, the path which is plotted out by the phasors on the Argand diagram of FIG. 1b will be known as the "frequency tracking locus". A real time plot of the frequency tracking locus, for example on a computer screen, can provide the clinician with valuable information concerning the particular system being monitored, in particular in the present example with information on the interactions between the spontaneous respiration of a patient and the respiration provided by means of a mechanical ventilator.

Figure 2A:
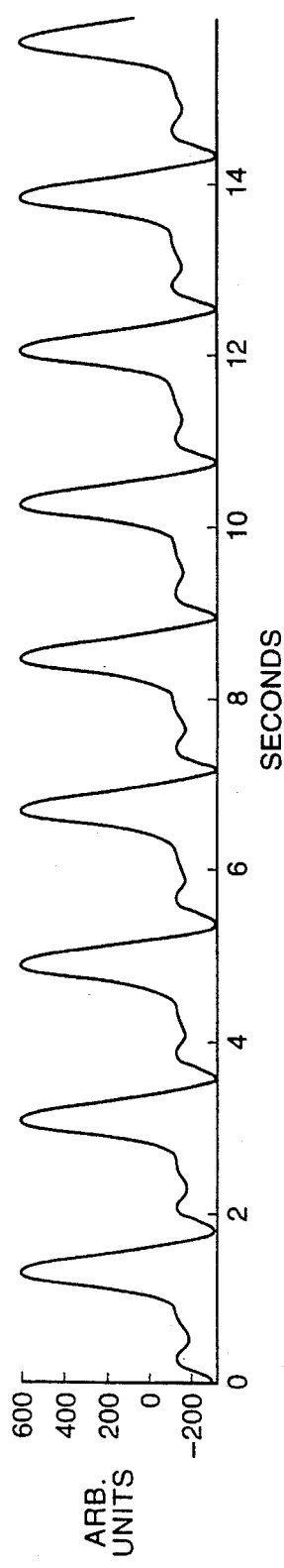
FIGS. 2a and 2b show a typical output from a respiratory monitoring system.
Figure 2B:
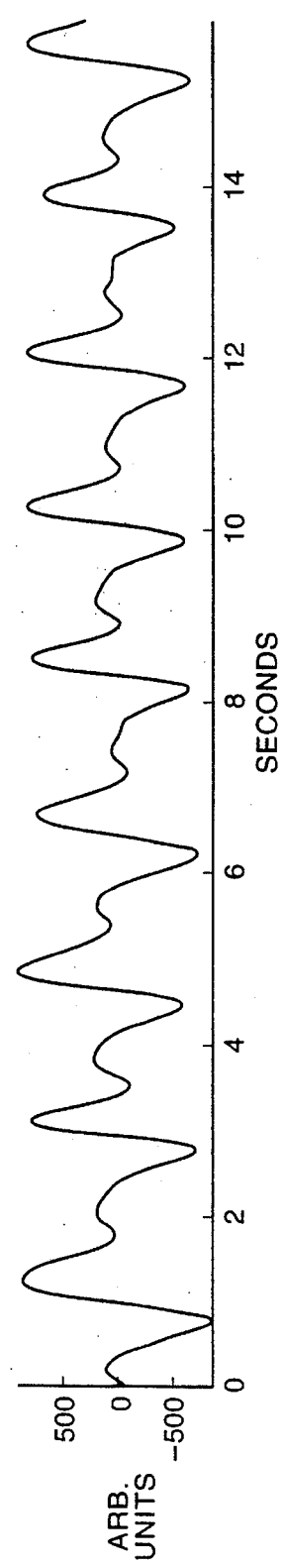
Figure 2C:
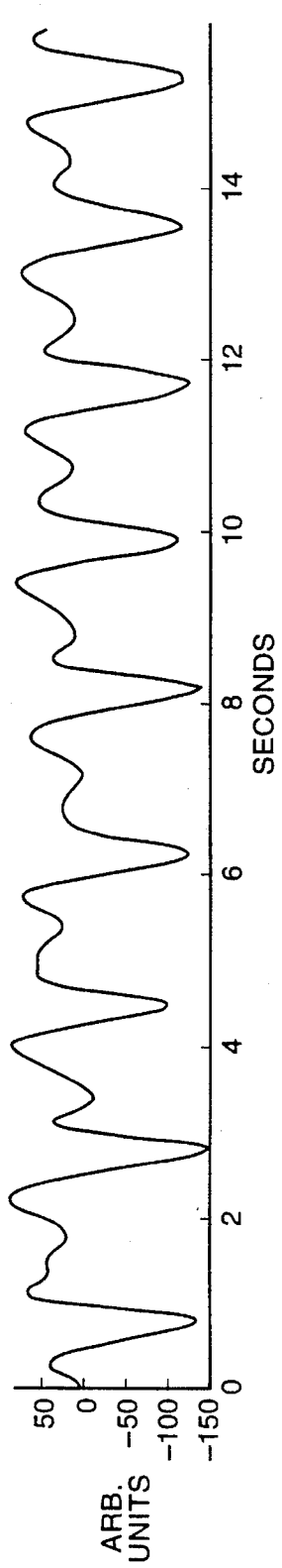
FIG. 2C shows a reconstructed oesophgeal pressure signal.

In order to test the invention, the frequency tracking locus was applied to data recorded from two preterm infants undergoing mechanical ventilation during intensive care. Airway pressure was measured at the proximal airway, and oesophageal pressure was measured using a 4 cm long balloon in the mid-oesophagus, both being transduced via Gaeltec pressure transducers. Signals were band-pass filtered and were recorded on FM tape for later digital analysis. Airway pressure (FIG. 2a) represents the input to the non-linear oscillatory activity of the respiratory centre, and is deterministic, the babies in both examples being ventilated using a time-cycled, pressure-limited ventilator at a constant rate and pressure which was determined by clinical considerations. Oesophageal pressure (FIG. 2b) represents the output from the process, the raw data consisting of elements derived from passive ventilation in the absence of spontaneous respiratory effort, and spontaneous respiration itself. In order to separate the effects of active inspiratory effort from those of passive lung inflation an ensemble average of oesophageal pressure data was calculated over 100–500 airway pressure cycles. This ensemble was subtracted from the raw oesophageal pressure data to give the best estimate of active inspiratory effort, as shown in the reconstructed oesophageal pressure signal (FIG. 2c).

Further details of the preferred method used for separating out the effects of active inspiratory effort from those of passive lung inflation will be described later. It should be noted that all the signals shown in FIGS. 2a–2c have been low pass filtered.

Once the signals have been ensemble averaged and low pass filtered, calculation of the frequency tracking locus can begin. The airway pressure signal is taken as the input signal of FIG. 1a, and the reconstructed oesophageal pressure signal as the output signal. The values of $M_i$ and $\Theta_i$ are then determined on a cycle by cycle basis.

Because neither the input signal nor the output signal are simple sinusoidal curves, appropriate detection algorithms are required to determine the defined points on the input and output signals between which the angle $\Theta_i$ is to be measured. One possibility is for the breath detection algorithm to select the maximal rate of fall in the reconstructed oesophageal pressure signal which is nearly coincident with the onset of diaphragmatic contraction (that is, the onset of spontaneous inspiration). The timing of this event is compared with the rise in airway pressure which marks the onset of inflation by the mechanical ventilator. The onset of spontaneous inspiration is compared with the onset of mechanical inflation which occurs within one half period of the ventilator cycle, and is converted to the phase angle $\Theta_i$, in degrees, as follows:

$$\Theta_i(\text{degrees}) = \frac{tV_i - tI_i}{tV} \cdot 180$$

Where $tV_i$ is the onset of mechanical inflation, $tI_i$ is the onset of spontaneous inspiration, and $$tV = \frac{1}{N-1} \cdot \sum_{n=2}^{N} (tV_n - tV_{n-1})$$

Determining the maximum rate of fall of the reconstructed oesophageal pressure signal is only one method of identifying the commencement of a cycle. In the preferred embodiment of the invention, the apparatus allows the user to select four separate algorithms to determine the start of each cycle. The methods are as follows:

(1) maximum turning point: the start of each cycle is identified simply as the point at which a maximum turning point occurs.

(2) minimum turning point: the start of each cycle is identified as the point at which a minimum turning point occurs.

(3) Downstroke: the maximum negative rate of change (maximum downstroke) over the entire signal sample is determined. The start of each cycle is then defined as the point at which the negative rate of change of the signal exceeds a user-defined percentage of the maximum downstroke.

(4) Upstroke: the maximum positive rate of change (maximum upstroke) over the entire signal sample is determined. The start of each cycle is then defined as the point at which the positive rate of change of the signal exceeds a user-defined percentage of the maximum upstroke.

In all cases, an amplitude rejection threshold is set by the user. This specifies a percentage of the mean of all individual cycle amplitudes. Any cycle whose amplitude is below this level is subsequently discounted and regarded as merely an unwanted minor turning point. In this way, any small dips or peaks in the signal may be ignored; for example, the small dips in FIG. 2c, between the main dips.

The reference signal (the airway pressure in this case) normally has a steady amplitude that enables the beginning of each cycle of the reference signal to be easily identified. A simple way of doing this is merely to define a threshold, and the beginning of each cycle is then determined as the point at which the signal crosses this threshold in a positive direction. The threshold may be set as a user-defined percentage of the maximum amplitude (for example, 10% or 20% of the maximum airway pressure amplitude).

Three examples will now be described, showing how the frequency tracking locus differs for stable and unstable states of baby-ventilator interaction.

EXAMPLE 1

Stable Interaction

During a stable period of mechanical ventilation (FIGS. 3a and 3b) the airway pressure signal (FIG. 3a) and the major downward deflections of the reconstructed oesophageal pressure record (FIG. 3b) are seen to be in a constant phase relationship. The frequency tracking locus over this period of 32 seconds reveals that the phasors lie close to the line of ideal entrainment, although minor phase changes still occur (FIG. 3c). The overall direction of the frequency tracking locus is at +125° (by convention, the output signal is said to "lead" the input signal by 125 degrees). The path length index is 1.034. Each ventilator inflation is accompanied by a spontaneous respiratory effort at a fixed phase relationship (1:1 entrainment). Noise in the oesophageal signal will be detected by the breath detection algorithm when its amplitude exceeds a given proportion of a true spontaneous inspiratory effort. Even when noise is wrongly interpreted as a spontaneous respiratory effort, however, the length of the phasor will be small, and contribute little to the overall path length index value.

EXAMPLE 2

Chaotic Interaction

Figure 4A:
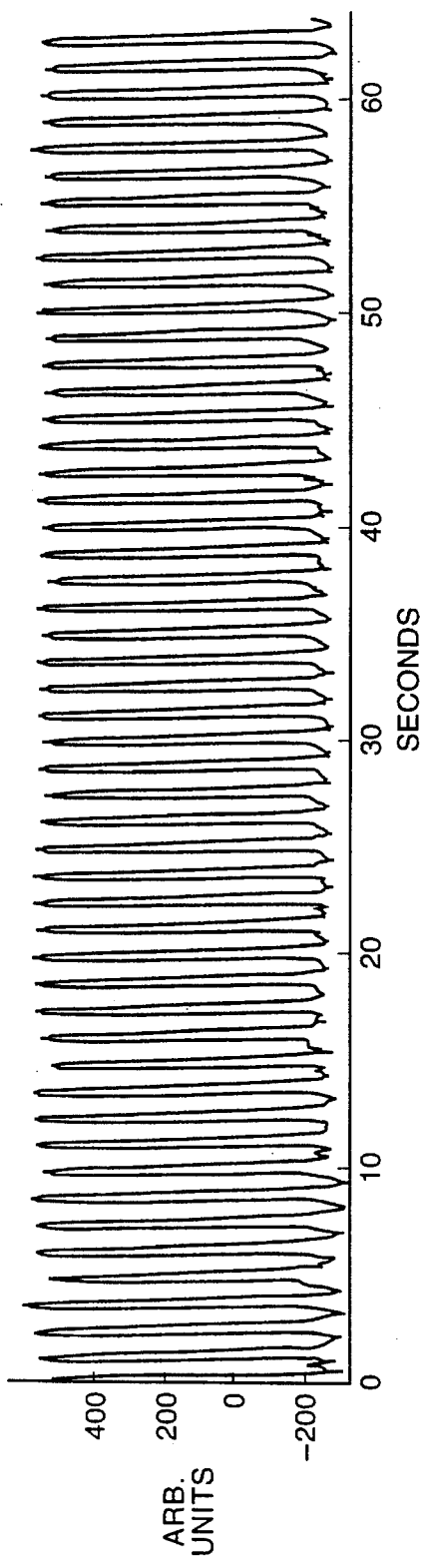
FIGS. 4a and 4b show airway pressure and oesophageal pressure during unstable mechanical ventilation in a preterm infant undergoing intensive care.
Figure 4B:
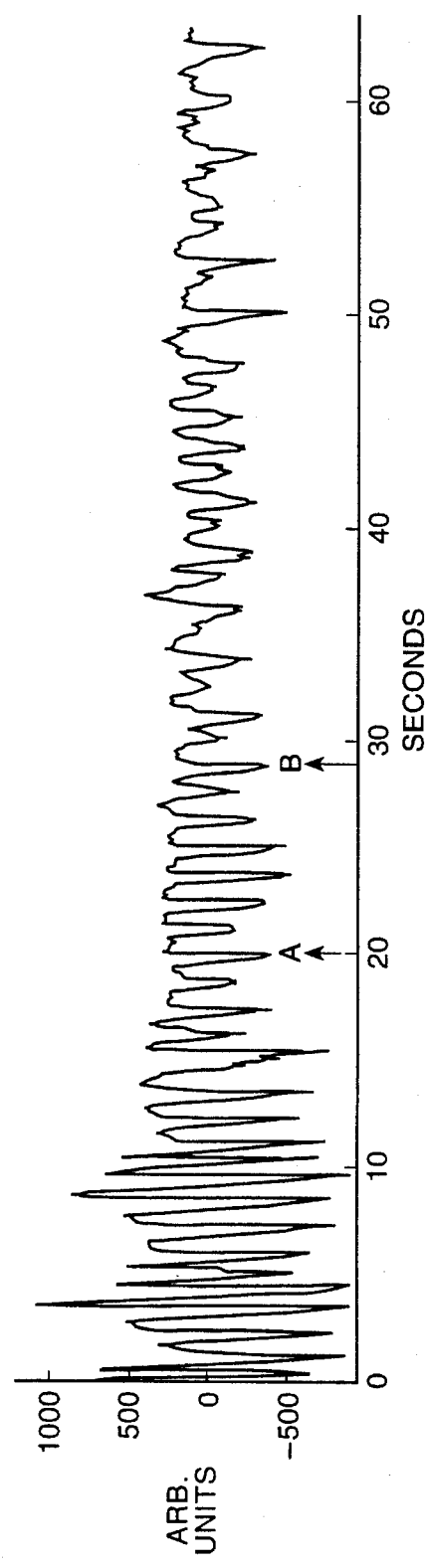
Figure 4C:
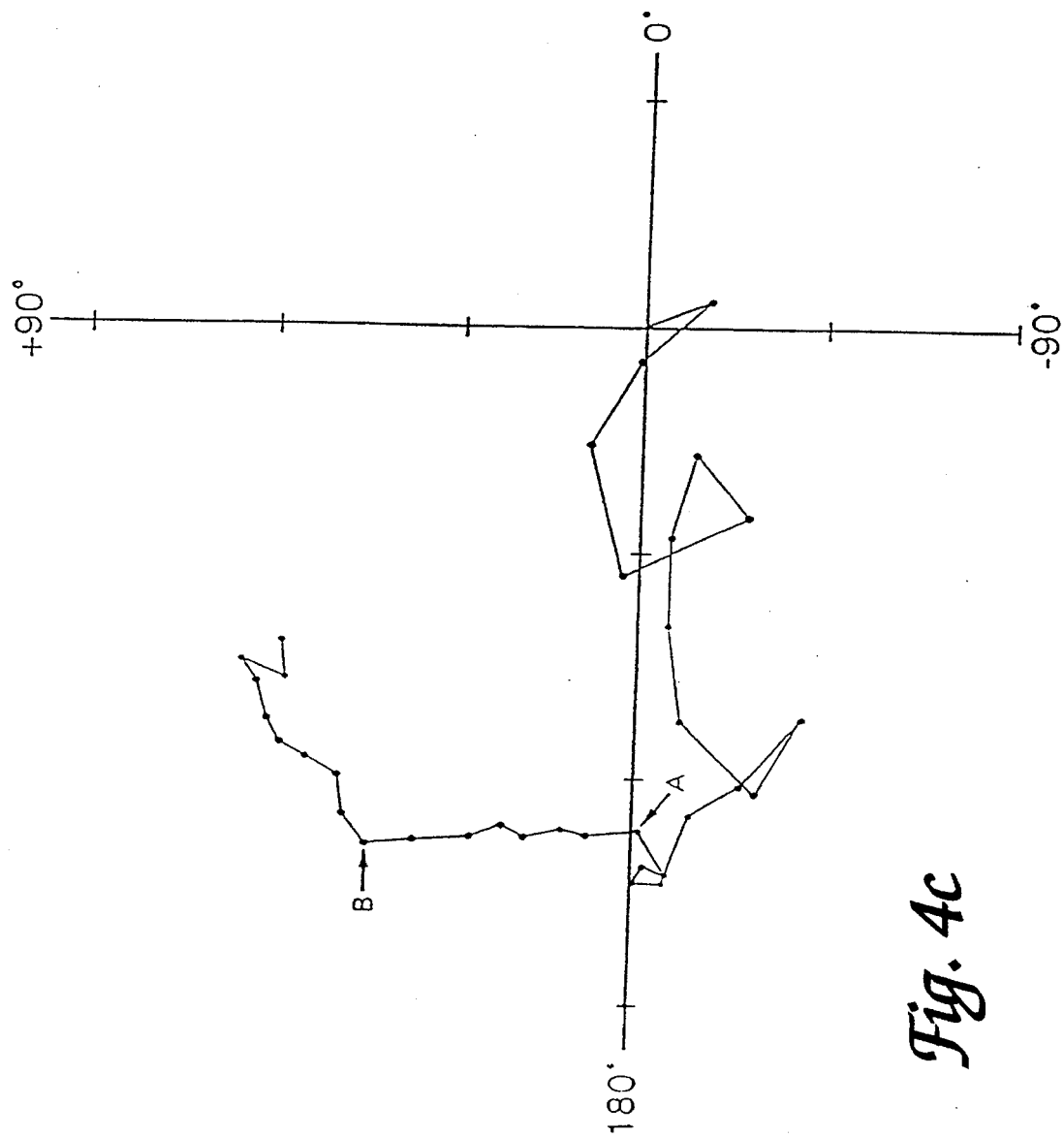

During highly unstable ventilation there is no readily discernible relationship between airway pressure and oesophageal pressure deflections (FIGS. 4a and 4b), although rapid changes in the rate of spontaneous breathing are apparent. The frequency tracking locus demonstrates three major features (FIG. 4c) i.e. phase jumps, relatively stable regions (e.g. region between points A and B) and chaotic regions. Variations in the length of the individual phasors are related to changes in the extent of spontaneous respiratory effort. The path length index is 4.172. Changing phase relationships reveal a lack of entrainment of spontaneous respiratory effort by the ventilator stimulus. In the example shown, there is a short period of unstable entrainment of spontaneous respiration by the mechanical ventilator between points A and B (arrowheads), which occurs in the overall direction of +90° and persists for seven spontaneous respiratory cycles.

EXAMPLE 3

Integer Ratio Entrainment During Low Rate Mechanical Ventilation

Figure 5C:
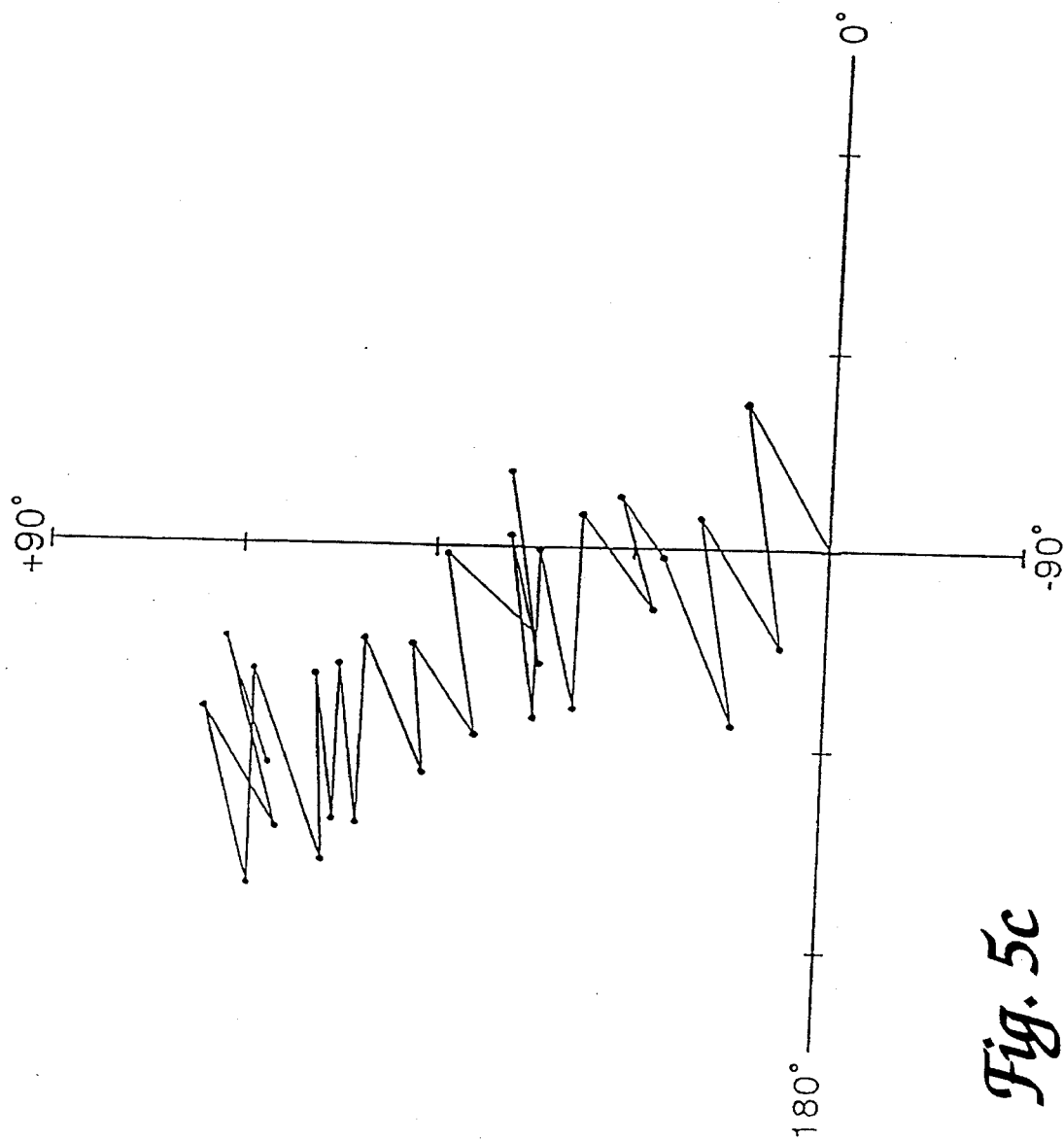

In this example an examination of the signals (FIGS. 5a and 5b) reveals that 32 spontaneous respiratory cycles are associated with 16 ventilator airway pressure cycles. Changes in both amplitude and in spontaneous respiratory rate can, however, be seen and are clearly seen in the frequency tracking locus description of the signals (FIG. 5c). The frequency tracking locus reveals an unstable 2:1 interaction where the overall direction of the locus varies and small changes in phase angle occur with each spontaneous respiratory effort. The path length index is 4.364. A "zigzag" course is typical of 2:1 interactions.

Typically, neonates are ventilated using pressure-limited, time-cycled ventilators at a fixed rate. During this form of ventilation, several different responses to individual inflations have been documented, namely apnoea, augmented inspiration, synchonous breathing, active expiration and reflex inhibition of inspiration. The effects of some of these types of response to mechanical ventilation upon the frequency tracking locus can be predicted. Apnoea or synchronous interaction will lead to an area of stability in the frequency tracking locus, which will tend to approach the line of ideal entrainment (e.g. FIG. 3c). Consecutive phasor lengths will be similar, as spontaneous respiratory amplitudes will be consistently low. The path length index will approach unity for these regions. The phase angle describing the frequency tracking locus will be close to zero degrees for apnoea and passive ventilation. We have found that 1:1 entrainment only occurs between ventilator stimulus and spontaneous respiratory effort in an individual infant during mechanical ventilation at a particular rate within a narrow range of phase angle: i.e. the overall direction of the frequency tracking locus will be constant during 1:1 entrainment, but the direction of the frequency tracking locus during 1:1 entrainment will be specific to an individual baby over a finite period e.g. example 2 (shown in FIG. 4c, between points A and B). When other phase relationships are apparent, 1:1 entrainment is not maintained.

Figure 5A:
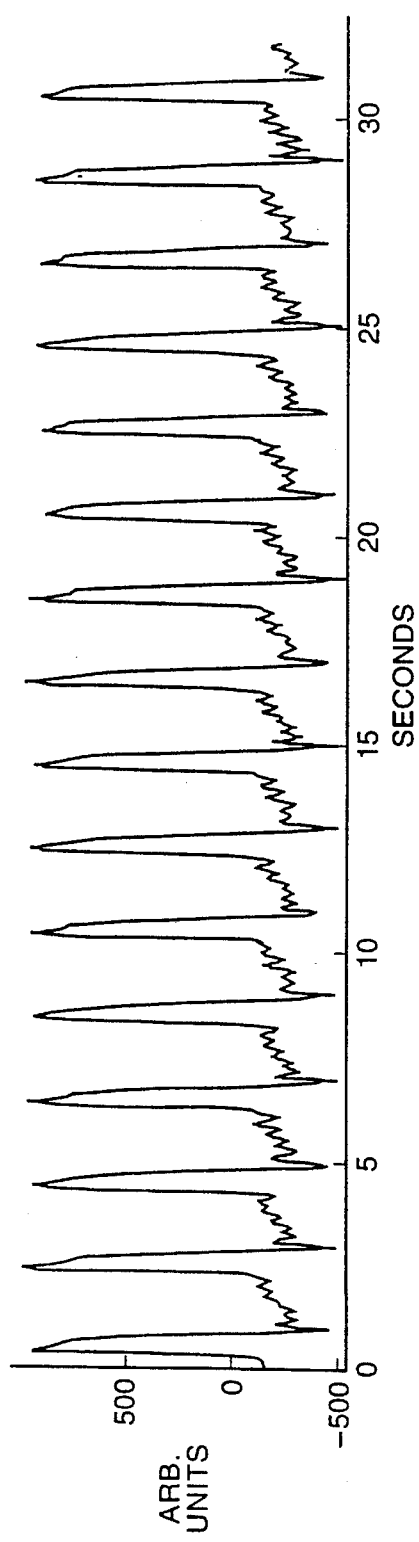
FIGS. 5a and 5b show airway pressure and reconstructed oesophageal pressure during complex baby-ventilator interactions.
Figure 5B:
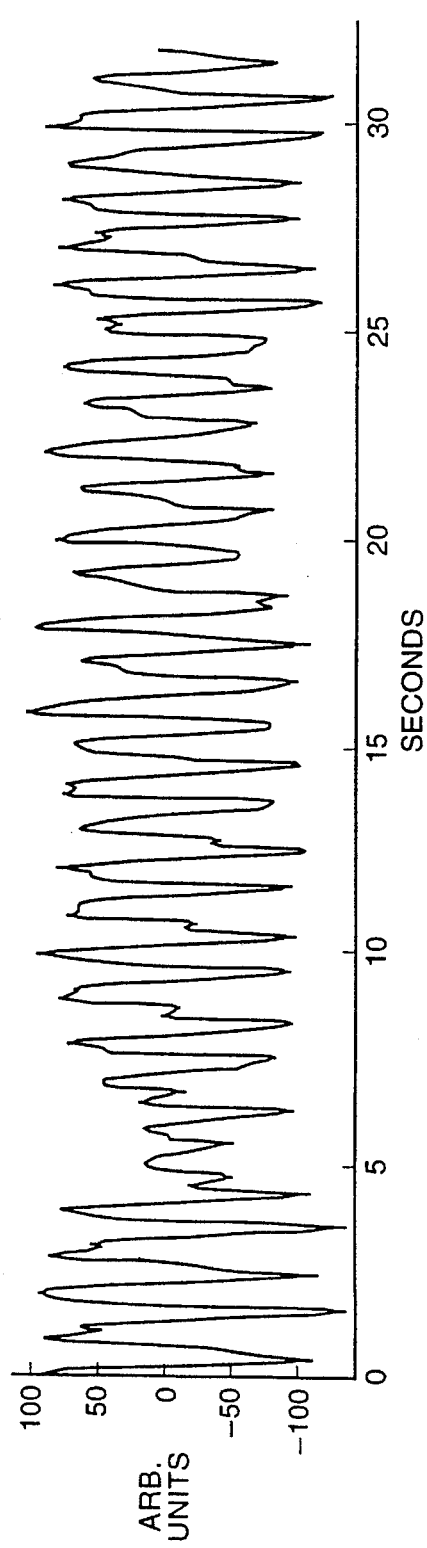

Reflex activity (or sudden, unpredictable activity such as gasps and hiccoughs) can be represented as a phase jump in the relationship between spontaneous respiratory activity and mechanical inflation. The path length index will be greater than unity for these areas. Reflex activity which affects the duration of spontaneous inspiration or expiration over multiple respiratory cycles (such as that occurring in Example 3, FIGS. 5a–5c) can be responsible for repetitive structures in the frequency tracking locus, but these are likely to be short-lived as the relative strength of each reflex is dependent upon several factors. Example 3 shows an expiratory prolongation reflex which regularly interferes with the spontaneous respiratory rhythm to induce a lengthening of the interbreath interval associated with each ventilator inflation (FIGS. 5a and 5b). This reflex interaction causes a 2:1 interaction.

In the above illustrations, the path length index is little affected by changes in relative magnitude when phase relationships are unvarying from cycle to cycle. The major effect on the path length index comes from changes in relative phase angle, and it is thus ideally suited to providing information about entrainment phenomena when stimulus and resultant frequencies are similar. When frequencies are widely different, the frequency tracking locus can describe polygonal paths and, thus, a very high path length index value can be obtained.

Phase jumps reflect the reflex response of one waveform (spontaneous respiratory effort) to individual cycles of the stimulus (the airway pressure signal), and the frequency tracking locus permits the recognition of reflex phenomena forming phase discontinuities. The frequency tracking locus is thus ideally suited to the description of respiratory entrainment phenomena in the clinical setting where the response to individual ventilator inflations and overall ventilatory strategy has to be assessed.

The system described herein gives clinicians a measure of the degree to which spontaneous breathing efforts by the patient are matched by the actions of the mechanical ventilator from breath to breath. The complex interactions between the patient and the ventilator are broken down to a single number representing the degree of chaos in the relationship between the patient's own breathing and the action of the mechanical ventilator. In the preferred embodiment, this number, the Path Length Index (PHI) is recalculated every 16 to 64 seconds, and is then displayed as a trend over several hours. The trend of the PLI can then be used to assess the effects of treatment (such as sedative drugs used to suppress the patient's own breathing) and changes in ventilation strategy (for example patient-triggered ventilation) upon the pattern of ventilation achieved.

The system may also display, for example on a computer screen, the progress of the frequency tracking locus (see FIG. 1b) over a period of several hours. The airway pressure and the reconstructed oesophageal pressure may also be displayed as individual traces, with or without low bandpass filtering and/or removal of noise and base line effects.

Figure 6:
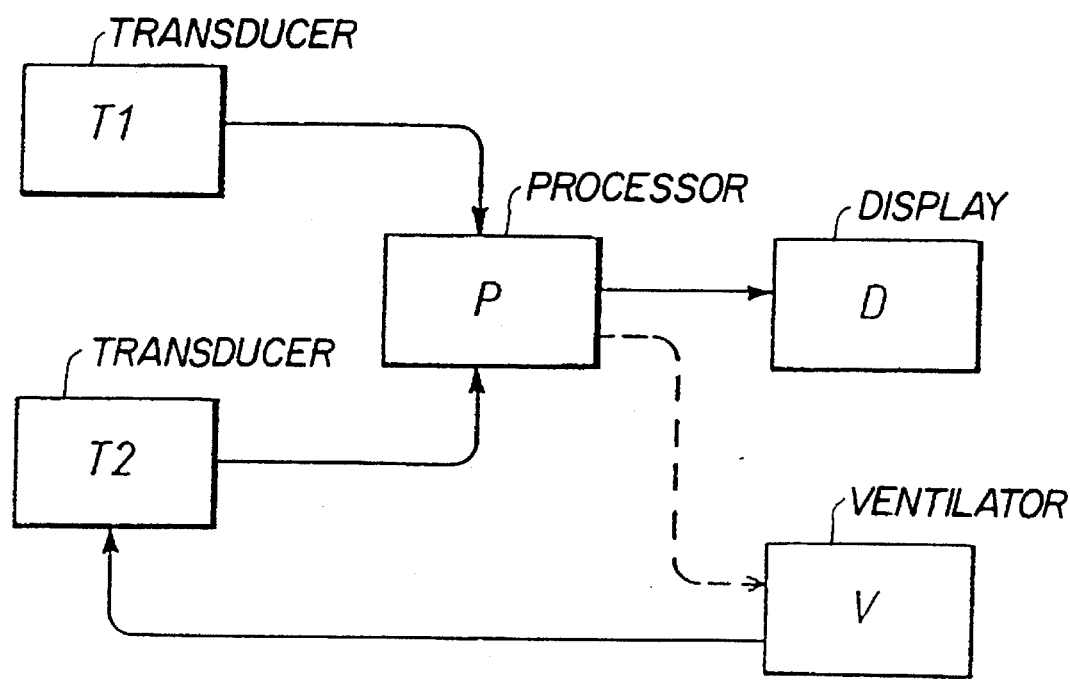
FIG. 6 shows in schematic form an embodiment of an apparatus in accordance with the present invention.

Turning now to FIG. 6, there is shown in schematic form an embodiment of apparatus in accordance with the present invention. A first transducer T1, which may be attached to a subject, produces a first electrical output signal dependent upon the respiration status of the subject. A ventilator V includes transducer means T2 to produce a second electrical signal which is dependent upon the ventilator inflation. The transducers are coupled to a processor P which includes signal comparator means to produce first and second control signals dependent upon the relative phase of signals from the first and second transducers and the ratio of the amplitudes of these signals. The display D is fed with the control signals and produces, amongst other things, a display of the frequency tracking locus of the transducer signals. As indicated above, the display may also show the raw transducer signals and/or the signals after filtering and removal of noise and base line effects. The incoming signals, specifically from the transducer means T1, will normally be low pass filtered to remove high frequency noise; that may be carried out by the processor P.

Optionally, the output of the processor P may be coupled to the ventilator, as shown by the dotted line in FIG. 6, so as to produce a feed-back path. In this way, the operation of the ventilator can be controlled in dependence upon the path length index, and perhaps also in dependence upon other features of the signals produced by the transducer means T1 and T2.

We have described a new form of measurement of total, chaotic activity in a system in which the stimulus and resultant signals are described in terms of phase and relative amplitude, cycle-by-cycle. We have demonstrated the application of this technique to a clinical situation in which complex interactions are known to be a prominent feature. The Frequency Tracking Locus can be used to provide a qualitative description of baby-ventilator interactions, and a quantitative description of changes in relative phase and amplitude (the Path Length Index) which corresponds to an "Index of Favourability" of ventilator strategy. This method allows clinicians caring for newborn infants to optimise mechanical ventilation for the individual by estimating the response to changes in therapy, such as the use of different ventilator rates, sedative agents and patient-triggered ventilation.

In the embodiment so far described, the output signal has been the reconstructed oesophageal pressure of the patient. Other methods for detecting spontaneous respiration could also be used, including inductance plethysmography, transthoracic impedance pneumography, diaphragmatic electromyogram and flow/volume signals from pneumotachography. Another convenient method is to attach an abdominal movement sensor (such as that used in apnoea monitoring). In each case, the output signal is then compared with the airway pressure signal from the ventilator circuit to the patient end, which is already available as an output from many modern ventilators.

In the embodiment of the apparatus in which there is no feedback from the processor to the ventilator (in other words where the dotted line shown in FIG. 6 is absent) it is necessary for the clinician to decide on the operating frequency of the ventilator. The optimal form of baby-ventilator interaction is generally thought to be a stable 1:1 relationship between spontaneous respirations and ventilator inflations so that each of the babies' breaths is accompanied by an artificial lung inflation. The difficulty, in the past, has been determining exactly which frequency to choose to produce the desired 1:1 entrainment. Previous studies have used a short period of disconnection from the mechanical ventilator in order to determine the spontaneous, unstimulated rate of respiration by the baby. This method does not take account of the interactions between the baby's own respiratory effort and the train of mechanical inflations. These interactions result from reflex activity caused by the stimulation of receptors within the lungs and chest wall when inflation occurs. Interactions are made more complex by the introduction of "noise" into the system from spontaneous motor and respiratory activity associated with clinical procedures and pain, and from unpredictable activity such as crying, gasps, sighs and hiccoughs.

Figure 7A:
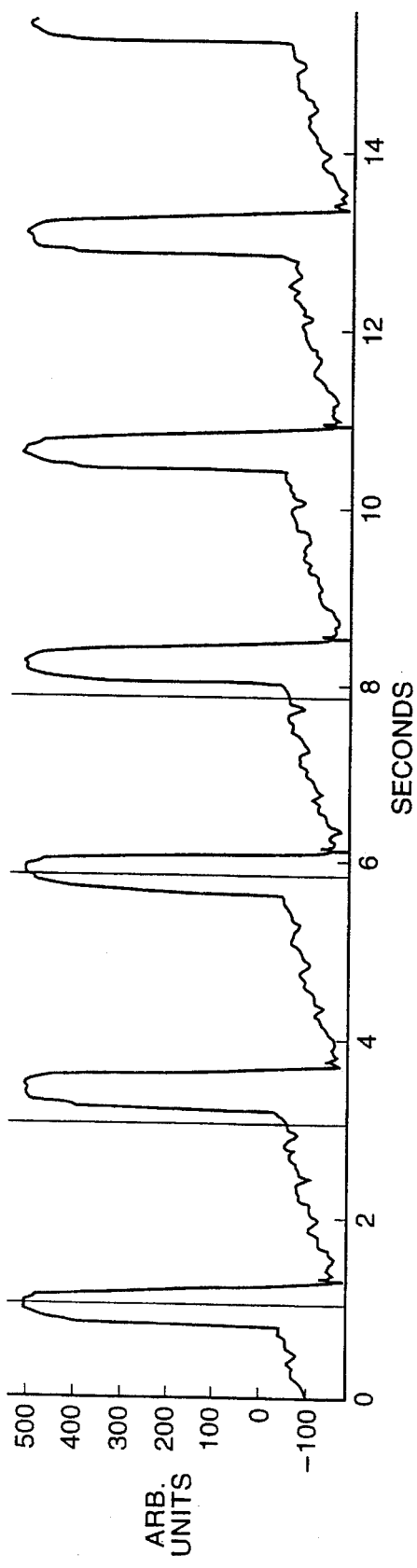
FIGS. 7a and 7b show airway pressure and oesophageal pressure during IMV illustrating the random association between spontaneous respiration and imposed lung inflations.
Figure 7B:
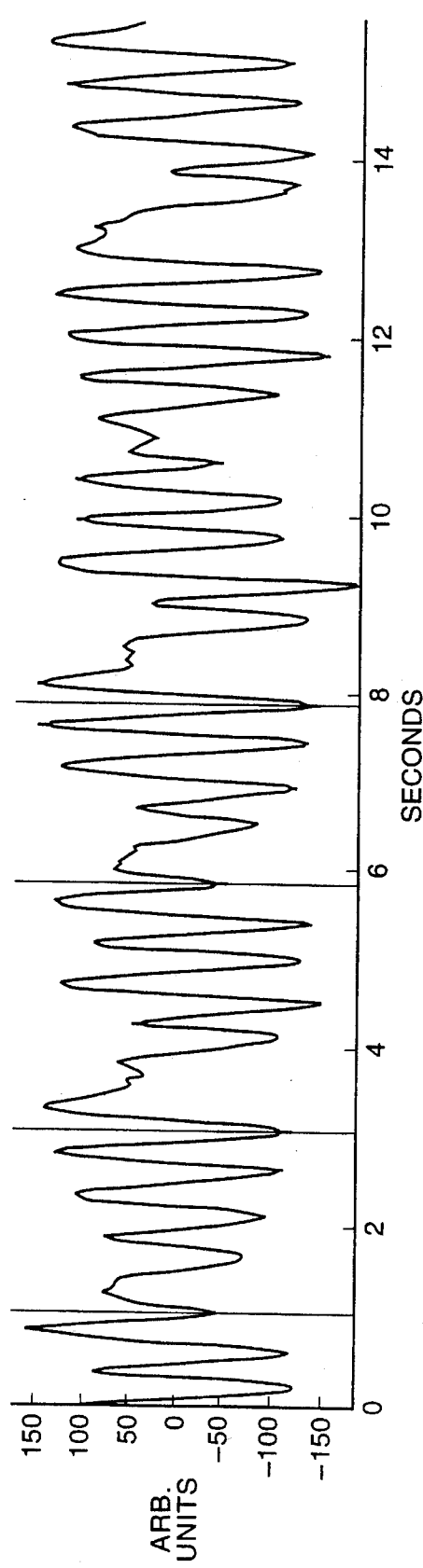

We have found from our research that it is possible to calculate the frequency at which 1:1 entrainment will take place by measuring the interval between spontaneous breaths during intermittent mandatory ventilation (IMV). Intermittent mandatory ventilation is illustrated in FIGS. 7a and 7b, the upper trace of which shows the airway pressure as forced by the ventilator at regular intervals. The lower trace shows the oesophageal pressure, and it will be seen that the baby is breathing relatively irregularly, but several times during each inflation cycle of the mechanical ventilator.

Once the oesophageal pressure signal has been averaged, the mean frequency is found to be a good guide as to the ventilator frequency at which the desired 1:1 entrainment will occur. Typically, the average frequency of spontaneous breath during IMV is not the same as the average frequency in the absence of external ventilation.

Any of the other alternative ways of determining active breathing, mentioned above, could also be used.

We will now describe the results of a research study which confirm that, with the present invention, the system has the ability to predict the rate at which a mechanical ventilator should be set in order to achieve a prolonged state of 1:1 entrainment.

20 infants were studied on 35 occasions during intermittent mandatory ventilation (IMV) when they were recovering from idiopathic respiratory distress syndrome. Orotrachael tubes delivered regular inflations at rates of ≦34/min via pressure-limited, time-cycled neonatal ventilators with inspiratory times and rates determined by clinical staff on the basis of blood gas measurements. The study was approved by the District Ethics Committee. Written parental consent was obtained in all cases.

Spontaneous respiratory timings were measured from an abdominal pressure capsule and, in some cases, compared with timings derived from oesophageal pressure measurements, transthoracic impedance, and surface diaphragmatic EMG. Oesophageal pressure was measured in the mid-oesophagus according to the method of Beardsmore et al. Oesophageal pressure measurements were not analysed when excessive peristaltic activity obscured the effects of spontaneous respiration. Airway pressure was measured from the proximal airway and abdominal capsule measurements were performed by using the Wright apnoea monitor according to the description of South. Diaphragmatic EMG signals were recorded on infants from bilateral skin electrodes placed over the anterior costal margin in right and left midclavicular lines. ECG artefact was subtracted using an R-wave triggered gate of length 40–100 msec and the output was via an root mean square (RMS) integrator with a time constant of 200 msec. Feedback from the RMS integrator output to the logic gate meant that the gate length window in the data was filled by averaged RMS output. The raw signal was delayed by 20–50 msec to centre the ECG complex in the gate period. The resultant diaphragmatic signal is referred to as RMS-EMG. Pulse oximeter values of arterial oxygen saturation and plethysmographic waveform were monitored throughout recordings (Nellcor N200).

Recordings were made during periods when infants were not crying and when gross motor movements were minimal. All infants were sedated with an opiate (pethidine) or chloral hydrate, given regularly as part of routine care within six hours of the start of recording. No attempt was made to formalise sleep staging because of the low gestational age of the infants and the presence of sedative agents which made meaningful descriptions of sleep state impossible. A period of 15 minutes was allowed between handling and the start of recording. Data were recorded on magnetic tape for periods of up to 2 hours. Analysis was performed off-line when recorded signals were played back through a low-pass filter (6 Hz cut-off) and underwent analogue-digital conversion of 16 Hz sampling rate. Arterial blood gases were taken shortly before the start of each recording and arterial PaCO2 was always between 35 and 45 mmHg. Arterial oxygen saturations lay between 90 and 96% for duration of recordings. No babies exhibited an arterial PH<7.35.

The most important methodological aspect of the study was the use of random fluctuations in spontaneous respiratory rate occurring against a background of deterministrically applied lung inflations at constant rate as shown in FIGS. 7a and 7b. Vertical bars in FIGS. 7a and 7b mark the inspiratory-expiratory juncture associated with each of the first four ventilator inflations: inflation occurs during both spontaneous inspiration and expiration. It will be seen, therefore, that lung inflation occurs at all phases of the spontaneous respiratory cycle so that the reflex response of the infant's respiratory system is interrogated during inspiration, expiration and also during transitions between these phases.

Figure 8:
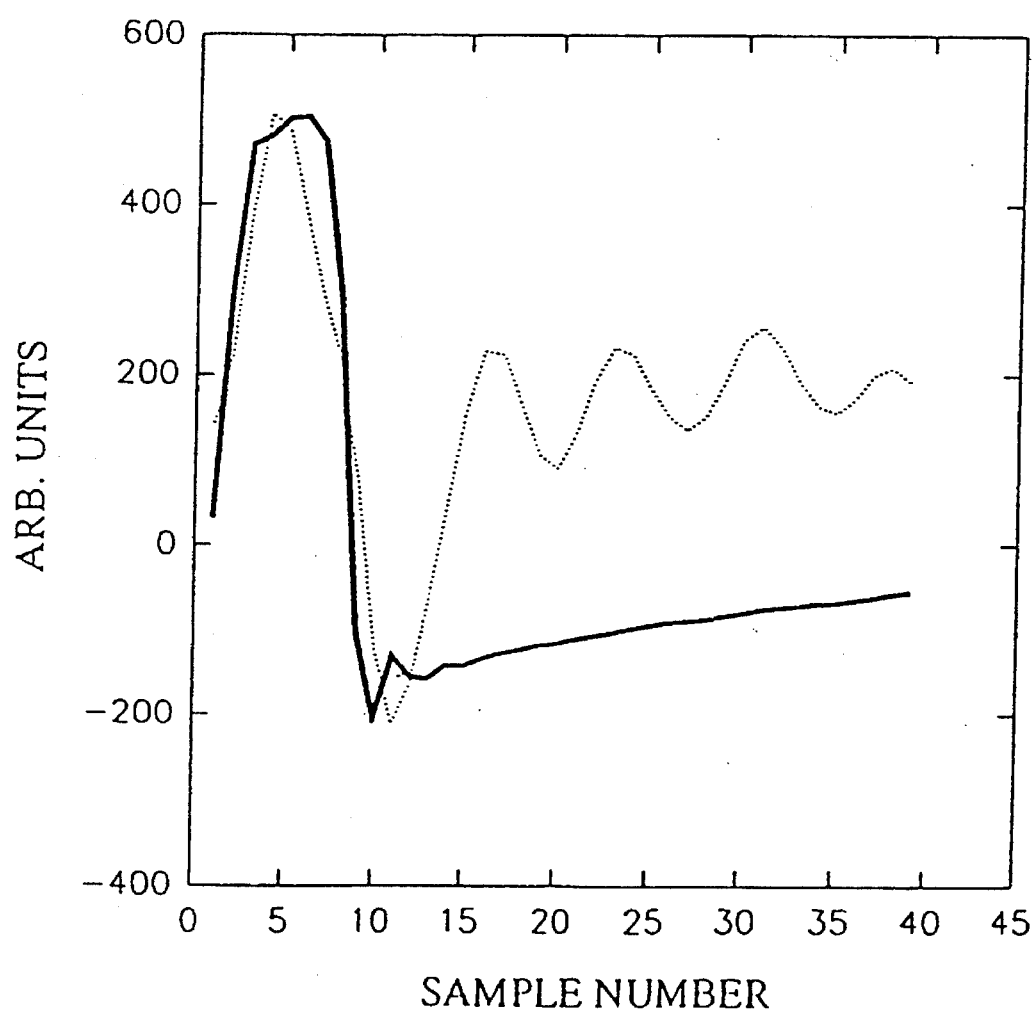
FIG. 8 shows the ensemble average over 300 ventilator cycles of airway pressure (bold line) and abdominal capsule (dotted line)

In order to separate the passive effects of mechanical lung inflation upon AC and OP (caused by the effects of inflation of the lungs causing a transmitted positive pressure) from the effects of spontaneous respiratory effort (caused by changes induced by descent of the diaphragm), an ensemble average of each of the waveforms was built up over 100–1000 ventilator inflations. FIG. 8 shows a typical ensemble average over 300 ventilator cycles of airway pressure (bold line) and abdominal capsule (dotted line). On average, there is a passive effect of inflation upon the abdominal capsule signal which then returns to the base line at a rate determined by the effective time constant of the circuitry. Further, damped oscillations occur which are due to interference by the cardiac impulse. As may be seen from FIG. 8, the abdominal capsule trace is nearly coincident with the airway pressure trace during mechanical inflation. The random distribution of spontaneous respiratory effects relative to ventilator inflation has led to the averaging out of spontaneous effort so that only the regular, passive component of the abdominal capsule signal due to mechanical inflation has remained. A similar result (not shown) is obtained if one determines the ensemble average of the oesophageal pressure trace. After calculation of the ensemble average the average was subtracted from the raw data for each ventilator inflation period in order to give an estimate of "active" respiratory components only (FIGS. 2a–2c).

In the subsequent description, the oesophageal pressure trace will be known as the OP trace, the abdominal capsule trace as the AC trace and the airway pressure trace as the AP trace.

In order to ensure that the ensemble averaging subtraction did not materially affect spontaneous respiratory timings in OP and AC traces when spontaneous breaths occurred in association with mechanical inflation, we compared the RMS-EMG signal with those of OP and AC before, and after subtraction of the ensemble average. Although mechanical (AC and OP and "neural" (RMS-EMG) respiratory timings were not identical, reflex prolongation of expiration was apparent in the RMS-EMG signal as well as in the reconstituted OP and AC signals: this phenomenon was not an artefact induced by the digital averaging and subtraction processes.

After subtraction of the passive, inflation-related component from OP and AC signals, AP OP and AC data were subjected to microcomputer-based algorithms which determined the onset and duration of mechanical inflation, the onset and end of each spontaneous inspiratory effort, and the intervals between all these events.

Spontaneous inspiratory duration, Ti, was defined as the period between the onset of a sharp fall in OP (or rise in AC) signal and the next minimum (maximum) in the signal provided that the apparent amplitude of inspiratory effort was greater than a preset limit. This limit was determined over the entire recording by automated algorithms. Spontaneous expiratory duration, Te, was defined as the period between the minimum (maximum) in the OP (AC) waveform and the next inspiratory downstroke (upstroke).

The breath detection algorithm selects the maximal rate of fall (rise) in the reconstructed oesophageal pressure (abdominal capsule) signal. We have confirmed that this event is nearly coincident with the onset of diaphragmatic EMG activity from careful examination of raw signals digitised at a sampling rate of 2000 Hz. The timing of this event was compared with the rise in airway pressure which marked the onset of inflation by the mechanical ventilator. In this way it was possible to differentiate between those spontaneous respiratory cycles any phase of which were associated with a ventilator inflation, from those spontaneous respiratory cycles which started and ended in the absence of any ventilator inflation.

All channels of reconstituted data (after subtraction of ensemble average) were processed in segments of 256 samples, which is the equivalent of 16 seconds of data at 16 Hz sampling rate.

Two methods were used concurrently in order to achieve maximum accuracy in the recognition of true, spontaneous respiratory effort.

(1) The first difference of the sampled data series, $\delta y$, was interrogated for each segment of 256 samples in order to derive the mean $\delta y$ for that segment. The segment was then scanned For regions of $\delta y$ in excess of a user-defined percentage (typically 10–20%) of mean $\delta y$ for the segment.

(2) The threshold for distinction between noise and a true spontaneous respiratory effort in the signal was set by detection of the turning points (maxima and minima) and calculating the difference in magnitude between successive turning points for the whole data segment.

For AC,TTI, and inductance plethysmography, a breath was deemed to have occurred when the first difference, $\delta y$, of the sampled data series was greater than a predefined percentage of the mean for that data segment and when the difference between the onset of inflation and the next maximum encountered is greater than a predefined proportion (typically 0.5–0.6) of the mean difference between successive maxima and minima as defined in (2) above.

For oesophageal pressure signals, where spontaneous inspiration is marked by a sudden fall in signal amplitude, a breath is deemed to have occurred when the first difference, $\delta y$, of the sampled data series is less than a predefined percentage of the mean for that data segment and when the difference in magnitude between the onset of inspiration and the next minimum encountered is greater than a predefined proportion (typically 0.5–0.6) of the mean difference between successive maxima and minima as defined in (2) above.

For the RMS-EMG and airway pressure signals, detection of spontaneous inspiration or mechanical inflation occurs when the signal attains an arbitrary, predefined value above the noisy baseline. The end of spontaneous inspiration or mechanical inflation is defined as that point when the signal falls below this threshold value. The maximum occurring in this region of the signal was then compared with the threshold for acceptance as a true breath or inflation according to (2) above.

Expiration is defined in all spontaneous respiratory channels as being the period between the end of one spontaneous inspiration and the onset of the next i.e. as the non-inspiratory period.

The major sources of artefact in the recognition of spontaneous inspiratory activity in the different data channels are:

(a) electromechanical noise (all channels) which causes baseline shifts and random fluctuations in respiratory timings: artefacts were avoided by averaging processes and setting thresholds for recognition of real events so as to exclude baseline shifts;

(b) spontaneous motor activity (all channels except AP) can be mistaken for respiratory effort: not specifically excluded, but avoided by setting upper limits of plausibility for respiratory timings;

(c) peristaltic activity and changes in physical disposition of sensor (OP only)—inherent problem in oesophageal ressure traces: avoidance as in (b) above;

(d) very rapid rates of respiration (all channels): rates above 3 Hz (rare) will be beyond the resolution of this system due to sensor and signal processing constraints;

(e) damped oscillations following activity (all channels)—due to filtering and "AC coupling" circuitry: avoided by use of ensemble averaging technique which displays, calculates and subtracts those effects from raw data signals (for all save DEMG);

(f) effects of analogue and digital filtering (all channels): as (d) above;

(g) sampling error (all channels): avoided by low-pass filtering at cut-off below Nyquist frequency; and (h) excessive humidity (AP only): clinical recognition.

Student's paired t-test was used to compare mean values of Ti, Te and IBI which were associated/unassociated with the inflation time of the mechanical ventilator for the duration of each recording in each subject.

Results—Effects of Lung Inflation on Respiratory Timings

Baseline Te was 0.48 s ($\pm 0.129$) and increased to 0.65 s ($\pm 0.182$, $p<0.0001$) when inflation was coincident with spontaneous respiration. Baseline Ti was 0.34 s ($\pm 0.062$ and increased to 0.38 s ($\pm 0.081$, $p<0.0001$) with inflation. IBI increased from 0.82 s ($\pm 0.161$, equivalent to 73/min) to 1.03 s ($\pm 0.201$, equivalent to 58/min) with inflation, an increase of 26%.

Prediction of Frequency for 1:1 Entrainment

Figure 3A:
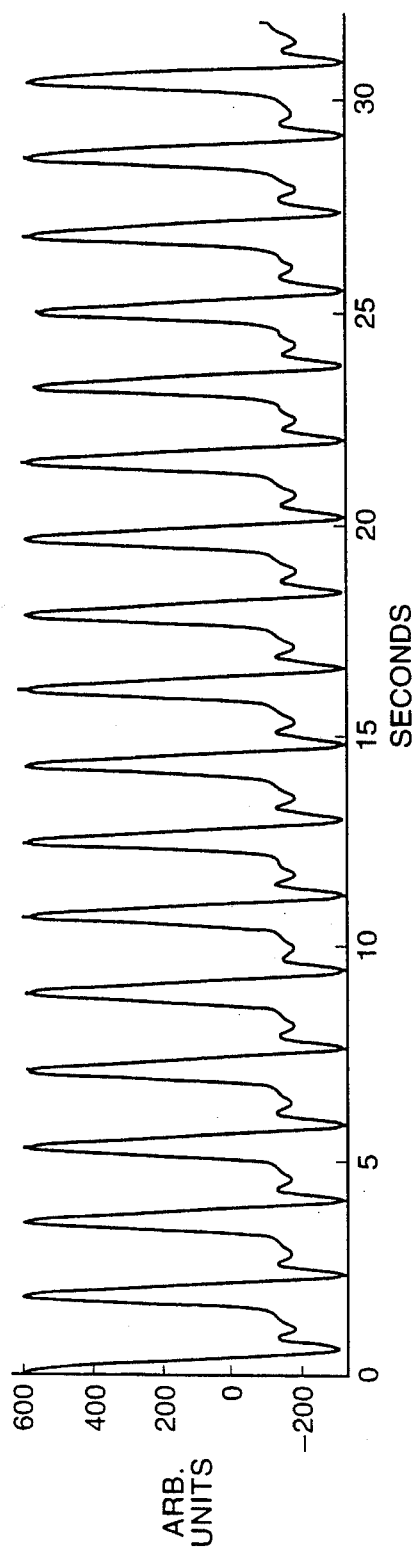
FIGS. 3a and 3b show airway pressure and reconstructed oesophageal pressure during stable 1:1 entrainment of spontaneous respiration by mechanical ventilation.
Figure 3B:
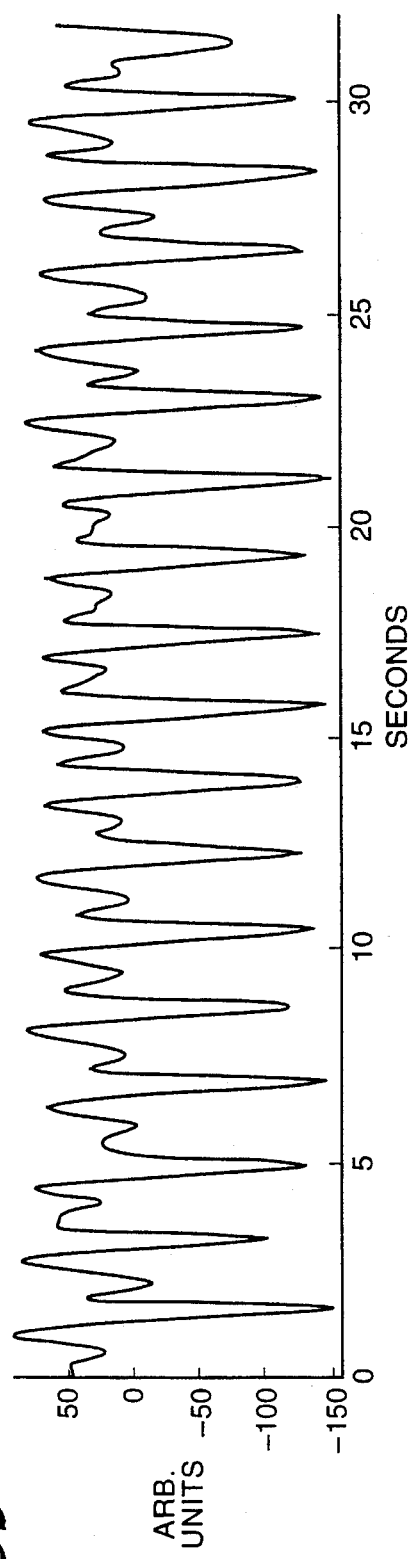
Figure 3C:
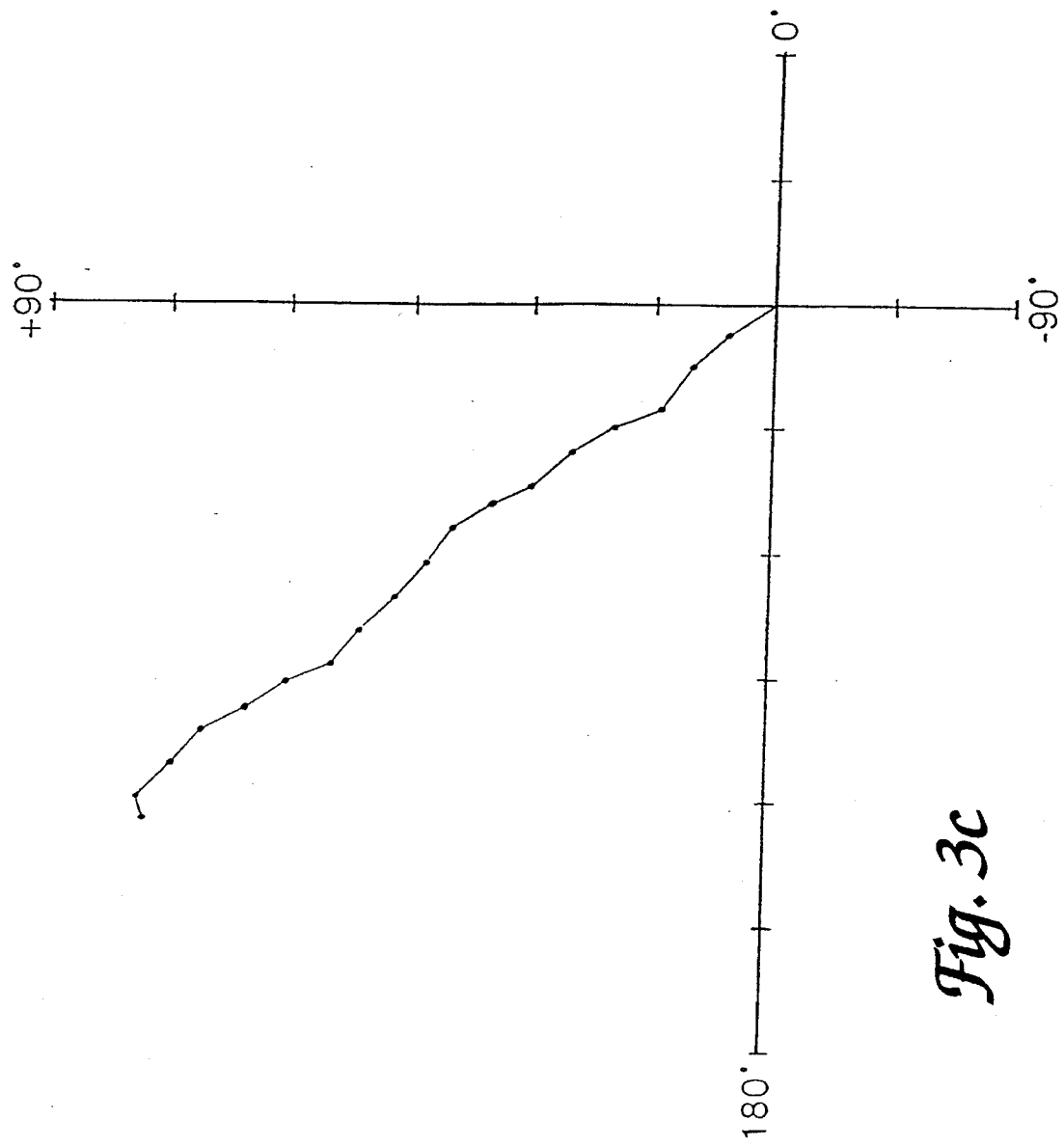

On several occasions, an increase in the rate of mechanical inflation to 50–60/minute resulted in 1:1 entrainment, characterised by a fixed phase relationship between inflation and spontaneous respiration in which mechanical inflation occurred at the end of inspiration, or early in expiration i.e. inflation and inspiration were out of phase (FIGS. 3a–3c). Unpredictable activity, such as gasps, were rapidly followed by a return to the phase-locked pattern. 1:1 entrainment of this type was seen for several hours. As ventilator rates fell with improved lung function, studies during IMV revealed that the rate of inflation to induce "stable" entrainment could only be predicted from the inter-breath interval (IBI (equivalent, on average, to a rate of 58/min) associated with inflations: during continuous positive airways pressure (CPAP) in the absence of mechanical lung inflations the spontaneous rate would be considerably higher (equivalent to 73/min, the overall average IBI of unassociated breaths above).

Figure 9A:
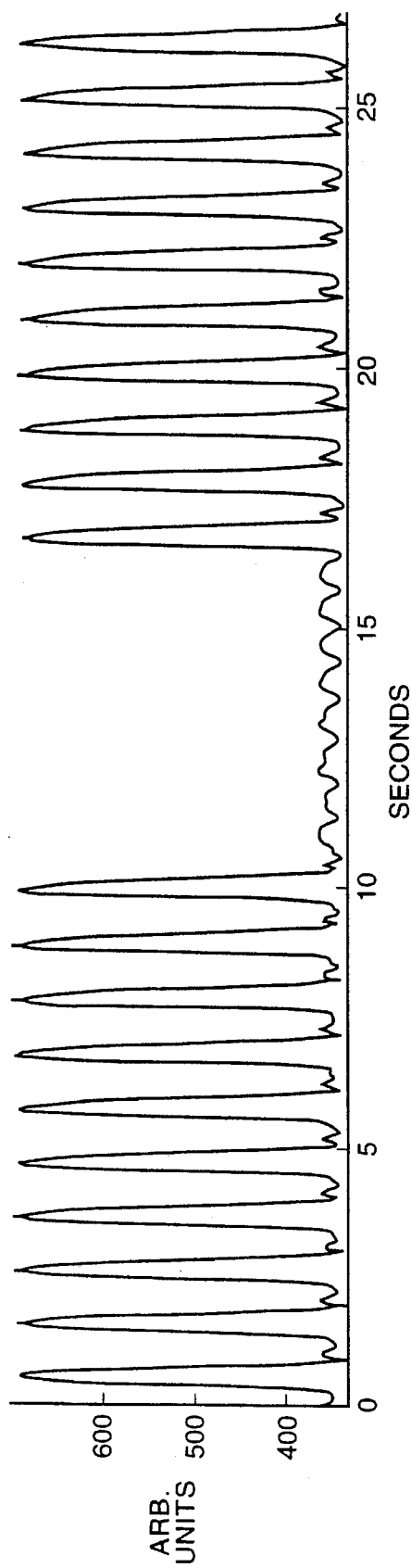
FIGS. 9a and 9b show airway pressure and RMS-EMG signals during 1:1 entrainment interrupted by a short period of continuous positive airways pressure.
Figure 9B:
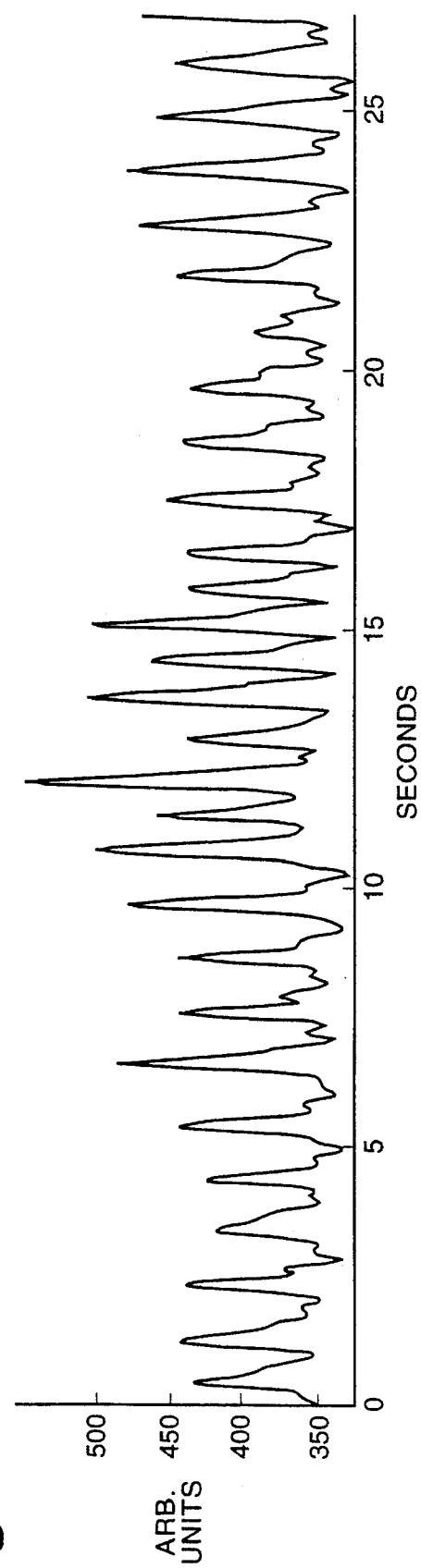

1:1 entrainment of spontaneous respiration could be induced at a rate which was predicted from the IBI during IMV, but not from the spontaneous respiratory rate in the absence of mechanical lung inflations. An example of an infant in a 1:1 entrained state at 57 inflations per minute who was switched to continuous positive airways pressure (CPAP) without inflations is given in FIGS. 9a and 9b. Note the immediate reversion to a higher, unstimulated rate of breathing of 79 breaths per minute when inflations are halted.

Pulmonary reflexes in the newborn have usually been investigated by the occlusion technique, and results from these studies may not be comparable with those from studies of lung inflation because of the effects of chest wall distortion on the intercostal phrenic inhibitory reflex. Despite early reports that the Hering-Breuer expiratory prolongation reflex diminishes with postnatal age, and was less active in preterm infants, more recent work confirms the findings of our study i.e. that expiratory prolongation reflexes are present even down to the lowest gestational ages and do not diminish over the first days and weeks of life.

Our results show that cases IBI was prolonged in all cases by the effects of mechanical inflation. IBI changes were dominated by changes in Te, and a strong correlation existed between IBI and Te in most of the cases studied. IBI was more prolonged for inflations occurring during the spontaneous expiratory phase than during spontaneous inspiration, the extent of IBI prolongation being proportional to the duration of expiration at the instant when mechanical lung inflation occurred. As spontaneous respiratory rate was largely determined by changes in Te, greater prolongation of IBI occurred when spontaneous respiratory rate was lowest.

Changes in Ti were less marked, but Ti usually increased when inflation occurred during the spontaneous inspiratory phase. This finding is in line with other studies of spontaneous respiratory timing in preterm infants, where the response to lung inflation does not switch off inspiratory drive, as it would in the adult, being apparently mediated in adults by a slowly reacting stretch receptor. The inspiratory prolongation which is seen in the preterm infant is thought to be due to the prevention of rib-cage distortion by diaphragmatic activity, hence eliminating another reflex, possibly the intercostal phrenic inhibitory reflex described by Byran et al, the effect of which will be to shorten inspiration.

Entrainment (phase-locking) of spontaneous respiration by rates of inflation less than the spontaneous rate must occur by slowing of the spontaneous rate of breathing. Previous descriptions of attempts to induce "phase synchrony" between mechanical ventilation and spontaneous respiratory activity have usually relied upon the observation of respiratory rates when the baby is switched from regular ventilation to CPAP for short periods. This method will not allow the effects of a train of inflations upon spontaneous respiration to be evaluated. Thus, the use of IMV induced reflex activity predicted the rate at which stable entrainment of spontaneous respiration could be achieved. Even during "stable entrainment", minor changes in spontaneous respiratory rate were occurring, but the effects of inflation-induced IBI prolongation reflexes were sufficient substantially to correct the subsequent IBI and maintain a 1:1 relationship.

It is clear from the above discussion that entrainment of spontaneous respiration in this way is only possible by rates of mechanical ventilation which are less than the spontaneous rate when unaffected by inflations.

As will be clear from the preceding descriptions, the apparatus embodying the present invention will desirably be capable of producing intermittent mandatory ventilation (IMV) for a certain period, and during that time have means for calculating the spontaneous inter-breath interval (IBI) of the patient. The apparatus should then either be automatically or manually switchable to produce continuous ventilation at a frequency at or about the IBI which has previously been determined. During an initialisation phase (for example ten minutes) the apparatus determines the average relationship between the input and output signals, following which the frequency tracking locus is displayed, along with the path length index (PLI) and the trend of the PLI. The input and output signals may also be displayed, after the subtraction of base line effects and noise. The averaging process may automatically be repeated, at defined intervals, for example every ten minutes.

What I claim is:

1. A device for monitoring a subject's physiological status comprising:

first transducer means for producing a first signal representative of the physiological status;

respiration apparatus having an effect on the physiological status;

second transducer means for producing a second signal representative of a cyclical status of said respiration apparatus; and processor means, coupled to receive said first and second signals, for producing an output signal dependent upon a relative phase of said first and second signals.

2. A device as claimed in claim 1, wherein said respiration apparatus is an artificial physiological stimulation apparatus including a mechanical ventilator, said device further comprising:

a respiration monitor, connected to said processor means, for displaying a respiration of said subject.

3. A device according to claim 2, wherein said first transducer means is a means for measuring spontaneous respiratory efforts of said subject.

4. A device according to claim 3, wherein said first transducer means includes an abdominal movement sensor.

5. A device according to claim 3, wherein said processor means comprises means for determining said subject's response to said external apparatus by subtracting an ensemble average of effects due to said mechanical ventilator from said first signal.

6. A device according to claim 5, wherein said processor means comprises means for automatically recalculating said ensemble average at periodic intervals, and for repeating said subtraction.

7. A device according to claim 3, wherein said processor means comprises means for determining a ratio of an amplitude of said first signal to an amplitude of said second signal.

8. A device according to claim 3, further comprising display means for displaying a frequency tracking locus of plotted phasors representing a relative difference between said first signal and said second signal.

9. A device according to claim 3, further comprising:

calculation means for calculating a path length index (PLI) determined from said relative phase of said first and second signals according to a formula $$PLI = \frac{1}{M_i} \sum_{n=1}^{k} M_n,$$

where n is a number of phasors, $M_i$ is a magnitude from an origin to a tip of said $k^{th}$ phasor, said phasors representing said relative phase of said first and second signals; and display means for displaying said calculated path length index.

10. A device according to claim 9, wherein said display means comprises means for displaying a trend of said PLI over a period of time.

11. A device according to claim 9, further comprising alarm means for actuating an alarm if said PLI goes outside a predetermined range.

12. A device according to claim 2, wherein said first transducer means includes an inductance plethysmograph.

13. A device according to claim 2, wherein said first transducer means includes a transthoracic impedance pneumograph.

14. A device according to claim 2, wherein said first transducer means includes a pressure sensor.

15. A device according to claim 2, wherein said first transducer means includes a diaphragmatic electromyogram device.

16. A device according to claim 2, wherein said first transducer means includes a pneumotachograph.

17. A device according to claim 2, wherein said second transducer means includes an airway pressure sensor.

18. A device according to claim 2, further comprising first filter means for low-pass filtering said first signal prior to receipt by said processor means.

19. A device according to claim 18, wherein said device further comprises second filter means for low-pass filtering said second signal prior to receipt by said processor means.

20. A device according to claim 2, further comprising feedback circuit means, coupled to said processor means and said mechanical ventilator, for controlling said mechanical ventilator in dependence on said relative phase of said first and second signals.

21. A device according to claim 2, further comprising feedback circuit means, coupled to said processor means and said mechanical ventilator, for controlling said mechanical ventilator in dependence on a path length index (PLI), said path length index being determined from said relative phase of said first and second signals according to a formula $$PLI = \frac{1}{M_i} \sum_{n=1}^{k} M_n,$$

where n is a number of phasors, $M_i$ is a magnitude from an origin to a tip of said $k^{th}$ phasor, said phasors representing said relative phase of said first and second signals.

22. A method for monitoring a physiological status of a subject, said method comprising the steps of:
producing a first signal representative of the physiological status of said subject using first transducer means;
artificially respirating said subject with a respiration device to affect the physiological status of said subject;
producing a second signal representative of a cyclical status of said respiration device using second transducer means; and
producing an output signal which is dependent upon a relative phase of said first and second signals.

23. A method for monitoring a physiological status of a subject provided with artificial physiological stimulation, said method comprising the steps of:
producing a first signal representative of the physiological status of said subject;
producing a second signal representative of a cyclical status of said artificial physiological stimulation;
producing an output signal which is dependent upon a relative phase of said first and second signals; and
monitoring respiration of said subject.

24. A method according to claim 23, wherein said step of producing said first signal includes measuring spontaneous respiratory efforts of said subject.

25. A method according to claim 24, further including a step of measuring said subject's response to said artificial physiological stimulation by subtracting an ensemble average of effects due to said artificial physiological stimulation from said first signal.

26. A method according to claim 25, further including the steps of:
automatically recalculating said ensemble average at periodic intervals; and
repeating said subtraction.

27. A method according to claim 24, wherein said artificial physiological stimulation includes a mechanical ventilator, said method further including the steps of:
determining a frequency of said mechanical ventilator for a 1:1 entrainment with the said subject's spontaneous respiratory efforts by effecting an intermediate mandatory ventilation over a predefined period, and
determining said frequency according to a spontaneous inter breath interval during said period.

28. A method according to claim 24, wherein said output signal producing step produces said output signal in dependence upon a ratio of an amplitude of a spontaneous breath of said subject to an amplitude of said artificial physiological stimulation.

29. A method according to claim 24, further including a step of displaying a frequency tracking locus of plotted phasors representing a relative difference between said first signal and said second signal.

30. A method according to claim 24, further including a step of calculating and displaying a path length index (PLI), said path length index being determined from said relative phase of said first and second signals according to a formula $$PLI = \frac{1}{M_i} \sum_{n=1}^{k} M_n,$$

where n is a number of phasors, $M_i$ is a magnitude from an origin to a tip of said $k^{th}$ phasor, said phasors representing said relative phase of said first and second signals.

31. A method according to claim 30, further including a step of displaying a trend of said PLI over a period of time.

32. A method according to claim 30, further including a step of operating alarm means if said PLI goes outside a predefined range.

33. A method according to claim 23, wherein said artificial physiological stimulation includes a mechanical ventilator, said method further including a step of controlling said mechanical ventilator in dependence on said relative phase of said first and second signals.

34. A method according to claim 23, wherein said artificial physiological stimulation includes a mechanical ventilator, said method further including a step of controlling said mechanical ventilator in dependence upon a path length index (PLI), said path length index being determined from said relative phase of said first and second signals according to a formula $$PLI = \frac{1}{M_i} \sum_{n=1}^{k} M_n,$$

where n is a number of phasors, $M_i$ is a magnitude from an origin to said $k^{th}$ phasor, said phasors representing said relative phase of said first and second signals.

35. A method according to claim 23, further including a step of filtering said first signal.

36. A method according to claim 25, further including a step of filtering said second signal.

* * * * *